(12) United States Patent
Koh et al.

(10) Patent No.: US 6,673,800 B2
(45) Date of Patent: Jan. 6, 2004

(54) 4,5,-DIHYDROISOXAZOLYLAKYL-PIPERAZINE DERIVATIVES HAVING SELECTIVE BIOLOGICAL ACTIVITY AT DOPAMINE $D_3$ OR $D_4$ RECEPTOR, AND PREPARATION THEREOF

(75) Inventors: Hun Yeong Koh, Kyungki-do (KR); Kyung Il Choi, Seoul (KR); Yong Seo Cho, Seoul (KR); Ae Nim Pae, Seoul (KR); Jae Yang Kong, Daejeon (KR); Dae Young Jeong, Daejeon (KR); Sun Ho Jung, Seoul (KR); Ji Young Jung, Seoul (KR); Hee-Yoon Lee, Daejeon (KR)

(73) Assignees: Korea Institute of Science and Technology, Seoul (KR); Korea Research Institute of Chemical Technology, Daejeon (KR); Korea Advanced Institute of Science and Technology, Daejeon (KR)

( * ) Notice: Subject to any disclaimer, the term of this patent is extended or adjusted under 35 U.S.C. 154(b) by 119 days.

(21) Appl. No.: 09/838,253

(22) Filed: Apr. 20, 2001

(65) Prior Publication Data
US 2002/0107253 A1 Aug. 8, 2002

(30) Foreign Application Priority Data
Dec. 4, 2000 (KR) ........................................ 2000-73122

(51) Int. Cl.$^7$ .................... A61K 31/496; A61K 31/454; C07D 413/06
(52) U.S. Cl. ................. 514/254.04; 514/326; 544/367; 546/209
(58) Field of Search .................. 544/367; 546/209; 514/254.04, 326

(56) References Cited

U.S. PATENT DOCUMENTS

| | | | |
|---|---|---|---|
| 4,397,853 A | * 8/1983 | Kawakita et al. | 424/250 |
| 6,166,033 A | * 12/2000 | Nakazato et al. | 514/316 |

FOREIGN PATENT DOCUMENTS

| | | |
|---|---|---|
| WO | WO99/43670 | 2/1998 |
| WO | 98/15541 | * 4/1998 |

OTHER PUBLICATIONS

Hery et al. Medline Abstract for Encephale,vol. 19,pp. 525–532 (1993).*
Mason et al. Medline Abstract for Eur. J. Pharmacol.,vol. 221, pp. 397–398 (1992).*
"Advanced Organic Chemistry" by jerry March (2nd ed.), pp. 819–820.*
"Enantio– and Diastereocontrolled Dopamine D1, D2, D3 and D4 Receptor Binding of N–(3–Pyrrolidinylmethyl) benzamides Synthesized from Aspartic Acid", C Thomas et al., Bioorg. Med Chem Lett 9 (1999) pp. 841–846.
"4–Heterocyclylpiperidines as Selective High–Affinity Ligands at the Human Dopamine D4 Receptor", Journal of Medicinal Chemistry, 1997, vol. 40, No. 15, pp. 2374–2375.
"Substituted [(4–Phenylpiperazinyl)–methyl]benzamindes: Selective Dopamine D4 Agonists", Shelly A. Glase, et al., Journal of Medicinal Chemistry, 1997, vol. 40, No. 12 (1771–1772).

* cited by examiner

Primary Examiner—Emily Bernhardt
(74) Attorney, Agent, or Firm—Lowe, Hauptman, Gilman & Berner, LLP

(57) ABSTRACT

The present invention relates to 4,5-dihydroisoxazolylalkylpiperazine derivatives having selective biological activity at dopamine $D_3$ and $D_4$ receptors represented by the following Formula (1), and its preparation method through reductive amination reaction in the presence of reducing agent,

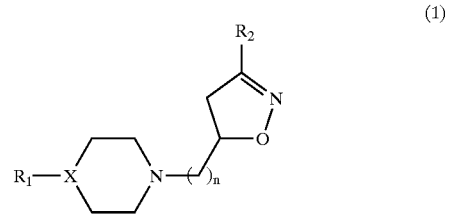

(1)

wherein $R_1$, $R_2$, X and n are the same as defined in the specification.

5 Claims, 1 Drawing Sheet

4,5,-DIHYDROISOXAZOLYLAKYL-PIPERAZINE DERIVATIVES HAVING SELECTIVE BIOLOGICAL ACTIVITY AT DOPAMINE $D_3$ OR $D_4$ RECEPTOR, AND PREPARATION THEREOF

BACKGROUND OF THE INVENTION

Field of the Invention

The present invention relates to 4,5-dihydroisoxazolylalkylpiperazine derivatives having selective biological activity at dopamine $D_3$ or $D_4$ receptors represented by the following formula (1), and its preparation method through reductive amination reaction in the presence of a reducing agent,

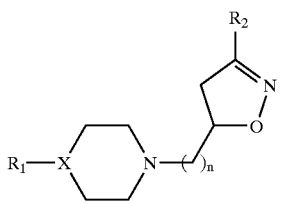

(1)

wherein $R_1$ represents aryl, arylalkyl, diarylalkyl, and heteroaryl, where the aryl groups may have one or more substituents selected from $C_1$–$C_6$ alkyl, $C_1$–$C_6$ alkoxy and a halogen atom, for example, phenylmethyl, diphenylmethyl, (2-trifluoromethylphenyl)methyl, phenyl, 2-methylphenyl, 2-methoxyphenyl, 3-methoxyphenyl, 2-ethoxyphenyl, 2-fluorophenyl, 4-fluorophenyl, 2-chlorophenyl, 4-chlorophenyl, 2-pyrimidyl, 4-chlorobenzhydryl, or 4,4'-difluorobenzhydryl group;

$R_2$ represents aryl, arylalkenyl and heteroaryl group, where the aryl groups may have one or more substituents selected from a halogen atom, nitro, $C_1$–$C_6$ alkyl and $C_1$–$C_6$ alkoxy group, for example, phenyl, 4-fluorophenyl, 4-chlorophenyl, 3-nitrophenyl, 2,4-dimethoxyphenyl, 3,4-dimethoxyphenyl, 3-phenoxyphenyl, styryl, 2-thienyl or 2-thiazol group X represents CH or a nitrogen atom; and n represents 3 or 4.

Dopamine is a neurotransmitter found in the brain of animals including human, which is indispensable in the transmission of nerve signals. The dopamine antagonist inhibits the binding of dopamine and dopamine receptor as an antipsychotic, and it is used for the treatment of mental disorder like schizophrenia.

According to recent publications, there are more than one type of dopamine receptors that function through G-protein, and some dopamine antagonists inhibit one type of dopamine receptor preferentially to the others. As the representative dopamine receptors early found, there are $D_1$ receptor that induces the activation of adenylyl cyclase and $D_2$ receptor that inhibits it. Afterwards totally 5 dopamine receptors were found, and they have been classified into two groups: $D_1$ group ($D_1$ and $D_5$) and $D_2$ group ($D_2$, $D_3$ and $D_4$).

Mental disease is related with central dopaminergic nerve system, and central postsynaptic receptor antagonists or presynaptic receptor (autoreceptor) agonists can be used as antipsychotics. Especially the $D_2$ group receptor antagonist haloperidol, a typical antipsychotic, gives extrapyramidal side effect (EPS) in case of long-term treatment. Such side effects occur from hypersensitive reaction due to the long-term inhibition of central dopamine receptor, and include involuntary movement (tardive dyskinesia) and hyperprolactinaemia caused by the inhibition of dopamine receptor at the pituitary gland. On the other hand, the antagonists that selectively act on dopamine $D_3$ or $D_4$ receptors are known to have no side effects like extrapyramidal side effect and tardive dyskinesia.

Accordingly, in the treatment of mental disease like schizophrenia, development of drugs having few side effects, i.e. new compounds that selectively acts on dopamine $D_3$ or $D_4$ receptor is of great importance.

SUMMARY OF THE INVENTION

As a result of the efforts to develop novel chemical compounds that selectively act on dopamine $D_3$ or $D_4$ receptors, the inventors found that novel compounds obtained by introducing various substituents to 4,5-dihydroisoxazolylalkylpiperazine skeleton have superior and selective antagonistic activity against dopamine $D_3$ or $D_4$ receptors.

Accordingly, the present invention aims at providing novel compounds useful for the treatment of mental disease, preparation methods thereof and pharmaceutical compositions containing them respectively as effective components.

DETAILED DESCRIPTION OF THE INVENTION

Figure 1:
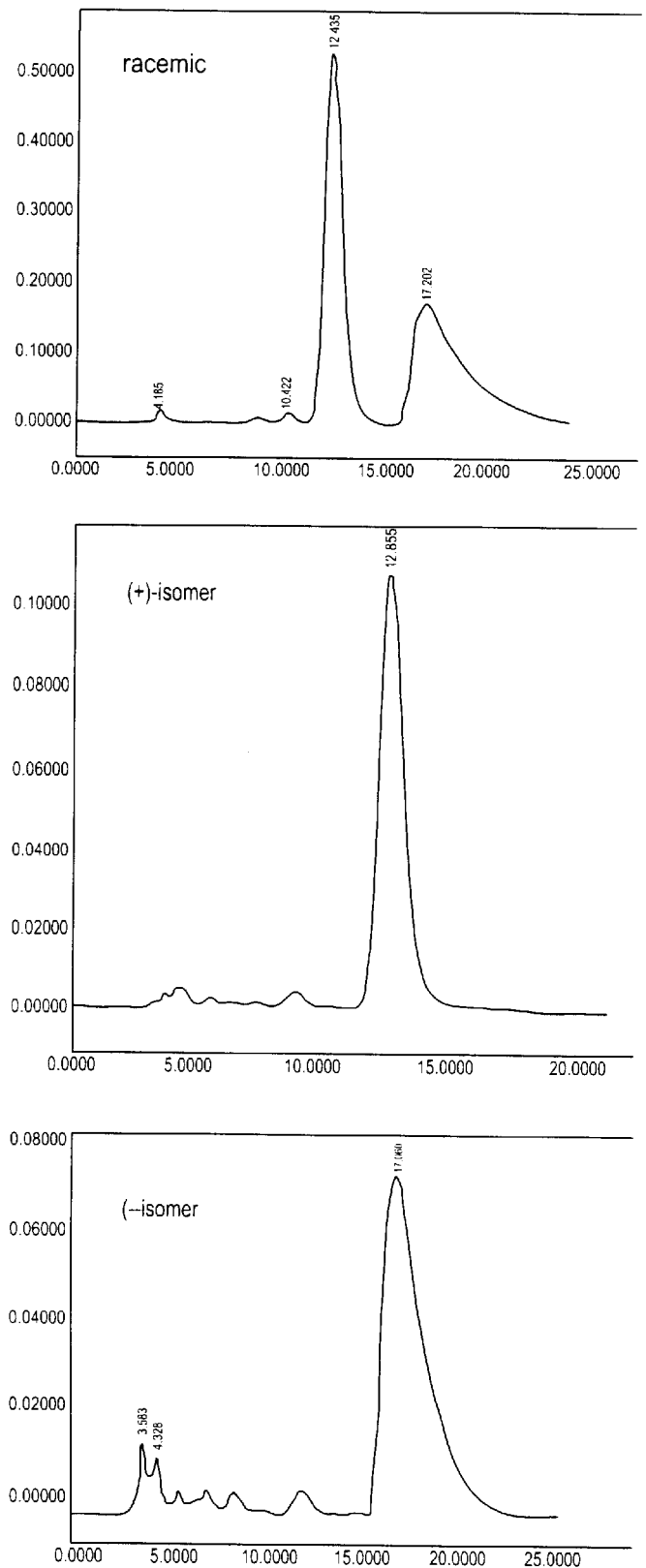
FIG. 1 is the HPLC chromatogram of the compound represented by formula (1) (Compound No. 29).

The present invention is characterized by 4,5-dihydroisoxazolylalkylpiperazine derivatives represented by the following Formula (1) and their pharmaceutically acceptable addition salts, which have physiological activity on dopamine $D_3$ and $D_4$ receptors,

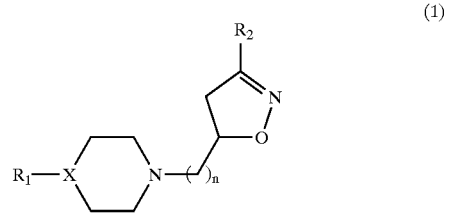

(1)

wherein $R_1$, $R_2$, X and n are the same as defined above.

4,5-Dihydroisoxazolylalkylpiperazine derivatives according to the present invention represented by formula (1) may have a chiral center, and they can exist as racemates or as mixtures of all possible isomers. Accordingly, the present invention includes racemates, respective isomers and mixture of isomers.

The present invention also includes radioactive 4,5-dihydroisoxazolylalkylpiperazine derivatives represented by formula (1), which are useful for the biological research.

4,5-Dihydroisoxazolylalkylpiperazine derivatives according to the present invention represented by formula (1) can be used to form pharmaceutically acceptable addition salts through common methods in the art. For example, nontoxic inorganic acids such as hydrochloric acid, hydrobromic acid, sulfuric acid, amidosulfuric acid, phosphoric acid or nitric acid; nontoxic organic acids such as propionic acid, succinic acid, glycolic acid, stearic acid, lactic acid, tartaric acid, citric acid, p-toluenesulfonic acid or methanesulfonic acid; pharmaceutically acceptable addition salts of these acids; or quaternary ammonium salts can be formed.

Hereunder is given a more detailed description about the substituents of 4,5-dihydroisoxazolylalkylpiperazine derivatives of the present invention represented by formula (1). 'Alkyl group' includes linear or branched carbon chains, and its specific examples are methyl, ethyl, propyl, isopropyl, butyl and t-butyl. 'Aryl group' includes a ring having at least 6 atoms, two rings having 10 atoms, or an aromatic ring stabilized by the resonance of the double bond of neighboring carbon atoms, and its specific examples are phenyl and naphthyl. This aryl group may have alkyl, alkoxy or phenoxy group as a substituent. 'Heteroaryl group' includes a single-ring aromatic group containing 5–6 atoms, which has more than one heteroatoms selected from the group consisting of N, O and S. Its specific examples are pyrrole, pyridine, oxazole, thiazole, furan and thiophene. It may have substituent like halogen atom, alkyl, amine and alkylamino group. 'Arylalkyl group' includes system having —$CH_2$— bonded to carbon of aryl group. Its specific example is phenylmethyl group (or benzyl group). 'Arylalkenyl group' includes system having —($C_2H_2$)—, a double bond, bonded to carbon of aryl group. Its specific example is styryl group. 'Diarylalkyl group' includes structure having —CH— bonded to each carbon of aryl group of two. Its specific examples are diphenylmethyl, 4-chlorobenzhydryl, 4,4'-difluorobenzhydryl groups.

In formula (1), it is preferable that $R_1$ is phenylmethyl, diphenylmethyl, phenyl or pyrimidyl group, wherein the aromatic ring may have one or more substituents selected from a halogen atom, $C_1$–$C_6$ alkyl and $C_1$–$C_6$ alkoxy; $R_2$ represents phenyl, phenethenyl, phenoxyphenyl or thienyl group, wherein the aromatic ring may have one or more substituents selected from a halogen atom, nitro, $C_1$–$C_6$ alkyl and $C_1$–$C_6$ alkoxy; X represents CH or a nitrogen atom; and n represents 3 or 4.

In formula (1), it is more preferable that $R_1$ is hydroxyl, diphenylmethyl, phenyl, 2-methylphenyl, 2-methoxyphenyl, 3-methoxyphenyl, 2-ethoxyphenyl, 2-fluorophenyl, 4-fluorophenyl, 2-chlorophenyl, 4-chlorophenyl, 2-pyrimidyl, 4-chlorobenzhydryl or 4,4'-difluorobenzhydryl; $R_2$ represents phenyl, 4-fluorophenyl, 3-nitrophenyl, 3,4-dimethoxyphenyl, 3-phenoxyphenyl, phenethenyl or 2-thienyl; X represents a nitrogen atom; and n represents 3 or 4.

Particularly preferable examples of 4,5-dihydroisoxazolylalkylpiperazine derivatives represented by formula (1) are as follows:

1-Benzhydryl-4-{3-[3-(4-fluorophenyl)-4,5-dihydroisoxazol-5-yl]propyl}piperazine;

1-Benzhydryl-4-{3-[3-(3-nitrophenyl)-4,5-dihydroisoxazol-5-yl]propyl}piperazine;

1-Benzhydryl-4-{3-[3-(3,4-dimethoxyphenyl)-4,5-dihydroisoxazol-5-yl]propyl}piperazine;

1-Benzhydryl-4-[3-(3-phenyl-4,5-dihydroisoxazol-5-yl)propyl]piperazine;

1-Benzhydryl-4-{3-[3-(3-phenoxyphenyl)-4,5-dihydroisoxazol-5-yl]propyl}piperazine;

1-{3-[3-(3-Nitrophenyl)-4,5-dihydroisoxazol-5-yl]propyl}-4-phenylpiperazine;

1-{3-[3-(3,4-Dimethoxyphenyl)-4,5-dihydroisoxazol-5-yl]propyl}-4-phenylpiperazine;

1-(2-Methoxyphenyl)-4-{3-[3-(3-nitrophenyl)-4,5-dihydroisoxazol-5-yl]propyl}piperazine;

1-{3-[3-(3,4-Dimethoxyphenyl)-4,5-dihydroisoxazol-5-yl]propyl}-4-(2-methoxyphenyl)piperazine;

1-(2-Methoxyphenyl)-4-{3-[3-(thiophene-2-yl)-4,5-dihydroisoxazol-5-yl]propyl}piperazine;

1-(4-Fluorophenyl)-4-{3-[3-(3-phenoxyphenyl)-4,5-dihydroisoxazol-5-yl]propyl}piperazine;

1-(2-Fluorophenyl)-4-{3-[3-(3-nitrophenyl)-4,5-dihydroisoxazol-5-yl]propyl}piperazine;

1-(2-Fluorophenyl)-4-{3-[3-(3-phenoxyphenyl)-4,5-dihydroisoxazol-5-yl]propyl}piperazine;

1-(2–Chlorophenyl)-4-[3-(3-phenyl-4,5-dihydroisoxazol-5-yl)propyl]piperazine;

2-(4-{3-[3-(3,4-dimethoxyphenyl)-4,5-dihydroisoxazol-5-yl]propyl}piperazine-1-yl)pyrimidine;

4-(4-Chlorophenyl)-1-[3-(3-phenyl-4,5-dihydroisoxazol-5-yl)propyl]piperidine-4-ol;

1-[3-(3-Phenyl-4,5-dihydroisoxazol-5-yl]propyl-4-(2-methylphenyl)piperazine;

1-[Bis(4-fluorophenyl)methyl]-4-{3-[3-(3-nitrophenyl)-4,5-dihydroisoxazol-5-yl]propyl}piperazine;

1-{3-[3-(3,4-Dimethoxyphenyl)-4,5-dihydroisoxazol-5-yl]propyl}-4-(2-ethoxyphenyl)piperazine;

1-(2-Ethoxyphenyl)-4-{3-[3-(thiophene-2-yl)-4,5-dihydroisoxazol-5-yl]propyl}piperazine;

1-Benzhydryl-4-{4-[3-(4-fluorophenyl)-4,5-dihydroisoxazol-5-yl]butyl}piperazine;

1-Benzhydryl-4-{4-[3-(3-nitrophenyl)-4,5-dihydroisoxazol-5-yl]butyl}piperazine;

1-Benzhydryl-4-{4-[3-(3,4-dimethoxyphenyl)-4,5-dihydroisoxazol-5-yl]butyl}piperazine;

1-Phenyl-4-[4-(3-phenyl-4,5-dihydroisoxazol-5-yl)butyl]piperazine;

1-{4-[3-(4-fluorophenyl)-4,5-dihydroisoxazol-5-yl]butyl}4-(2-methoxyphenyl)piperazine;

1-(2-Methoxyphenyl)-4-{4-[3-(3-nitrophenyl)-4,5-dihydroisoxazol-5-yl]butyl}piperazine;

1-{4-[3-(3,4-Dimethoxyphenyl)-4,5-dihydroisoxazol-5-yl]butyl}-4-(2-methoxyphenyl)piperazine;

1-(2-Methoxyphenyl)-4-{4-[3-(thiophene-2-yl)-4,5-dihydroisoxazol-5-yl]butyl}piperazine;

1-(2-Methoxyphenyl)-[4-(3-phenyl-4,5-dihydroisoxazol-5-yl)butyl]piperazine;

1-(2-Methoxyphenyl)-[4-(3-styryl-4,5-dihydroisoxazol-5-yl)butyl]piperazine;

1-(2–Chlorophenyl)-4-{4-[3-(thiophene-2-yl)-4,5-dihydroisoxazol-5-yl]butyl}piperazine;

1-[4-(3-Phenyl-4,5-dihydroisoxazol-5-yl)butyl]-4-(2-methylphenyl)piperazine;

1-{4-[3-(3,4-Dimethoxyphenyl)4,5-dihydroisoxazol-5-yl]butyl}-4-(2-ethoxyphenyl)piperazine; and pharmaceutically acceptable salts thereof.

The present invention also includes a preparation method of 4,5-dihydroisoxazolylalkylpiperazine derivative represented by formula (1), which can be illustrated by the following Scheme 1, Scheme 1

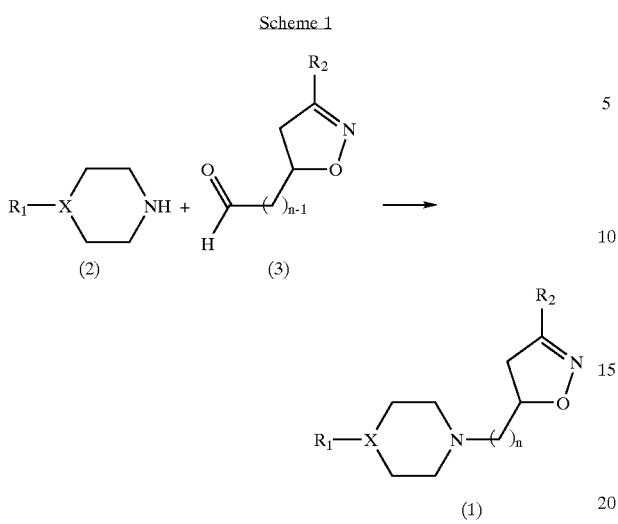

wherein $R_1$, $R_2$, X and n are the same as defined in formula (1).

As shown in Scheme 1, amine compound represented by formula (2) react with aldehyde compound in the presence of a reducing agent via amination reaction to obtain the compound represented by formula (1). The reductive amination reaction of the present invention is performed under a nitrogen atmosphere and at room temperature. Molecular sieve (4A, beads, 4–8 mesh) was used in the reaction, and 1–3 equivalents of glacial acetic acid may be added when the reactivity of the starting material is unsatisfactory. As the reducing agent for the imine formed by the condensation reaction of amine and aldehyde, $NaBH(OAc)_3$, $NaBH_3CN$ or $NaBH_4$ may be used, and its dosage is 2–10 equivalents depending on the reactivity and 2–3 equivalents are desirable. Common organic solvents can be used for the reaction solvent, and its specific examples are tetrahydrofuran, 1,2-dichloroethane, acetonitrile and methylene chloride. In the Examples of the present invention, mainly methylene chloride was used. The reaction time is 3–24 hr, and 12–14 hr is desirable. The reaction progress is traced using thin-layer chromatography (TLC). When the reaction is completed, saturated $NaHCO_3$ aqueous solution is added and the reactant is extracted with suitable organic solvent. For the extraction solvent, ether, methylene chloride and ethyl acetate can be used, and methylene chloride is best recommended.

The pharmaceutically acceptable addition salt of the compound represented by formula (1) can be prepared easily using common preparation method reported in the literature, and can be purified without special purification process. Hereunder is given a preparation method of a pharmaceutically acceptable addition salt of the compound represented by formula (1), attaching importance on the preparation process of a hydrochloric acid salt. After drying and evaporating the said extraction solvent, the residue is dissolved in small amount of ether followed by the addition of 1–10 equivalents of HCl ether solution to obtain a hydrochloric acid salt of the target compound in white solid form. As the solvent used in the preparation of HCl solution, chloroform, methylene chloride, ether, methanol, ethyl acetate or their mixture can be used, and ether is desirable. The product formed in white solid form can be separated with a centrifuge or a simple solvent removing device using cotton. After washing the solid 2–3 times with 1–2 mL of ether, it is dried to yield a hydrochloric acid salt as white solid with high purity.

Amine compound represented by formula (2), which is used as a starting material of the preparation method of the present invention, can be easily prepared by the methods reported in the literature. Aldehyde compound represented by formula (3), which is used as another starting material of the preparation method of the present invention, also can be easily prepared by the methods reported in the literature. The synthetic process can be illustrated by the following Scheme 2, Scheme 2

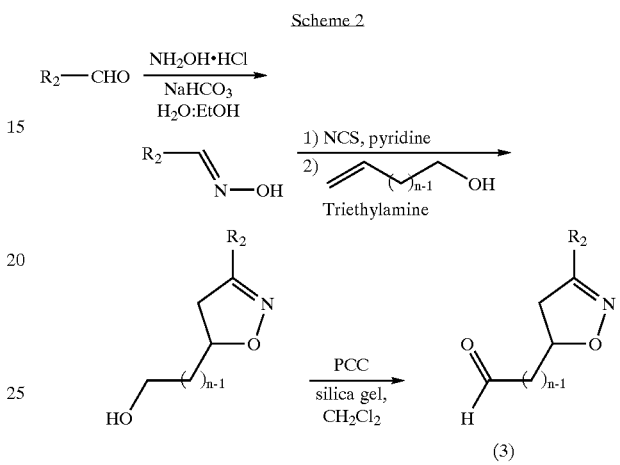

wherein $R_2$ and n are the same as defined in formula (1).

Since the 4,5-dihydroisoxazolylalkylpiperazine derivative according to the present invention, which is represented by formula (1), is very effective in the treatment of mental disease, the present invention includes the pharmaceutical compositions and the dopaminergic antagonists containing the novel compound represented by formula (1) as the effective component. The pharmaceutical compositions and the dopaminergic antagonists can be prepared in common oral or non-oral preparation form like tablets, capsules, troches, liquids and emulsions by adding common nontoxic pharmaceutically acceptable carrier, reinforcing agent and filler. The administration dosage of the compound represented by formula (1) depends on the age, weight, sex, administration type, health condition and disease progress of the patient, and for an adult patient with 70 kg of weight, the general dosage is 0.01–400 mg/day. It can be administered once a day or separately according to the direction of the doctor or pharmacist.

Hereunder is given a more detailed description of the present invention. However it should not be construed as limiting the scope of the present invention.

The following Comparative Examples are exemplary preparation methods of the amine compound represented by formula (2) and the aldehyde compound represented by formula (3), which are used as starting materials of the present invention.

COMPARATIVE EXAMPLE 1

Preparation of (3,4-Dimethoxyphenyl) hydroxyiminomethane

After dissolving 3,4-dimethoxybenzaldehyde (1.00 g, 0.081 mmol) in 60 mL of ethyl alcohol/water (1/1, v/v) solution, $H_2NOH$ HCl (0.54 g, 7.823 mmol) was added. While stirring the reaction mixture, $Na_2CO_3$ (0.83 g, 7.823 mmol) was added slowly at below 0° C. The reaction was continued for 1 hr in an oil bath preheated to 60–65° C. After the reaction was completed, 1.05 g (96.4%) of the target product was obtained by extracting with ethyl acetate, drying over anhydrous MgSO$_4$ and removing the solvent under reduced pressure.

COMPARATIVE 2

Preparation of 3-[3-(3,4-Dimethoxyphenyl)-4,5-dihydroisoxazol-5-yl]propan-1-ol (3,4-dimethoxyphenyl)(hydroxyimino)methane (1.05 g, 5.801 mmol) was dissolved in 30 mL of tetrahydrofuran under N$_2$. After adding N-chlorosuccinimide (0.93 g, 6.96 mmol) and pyridine (46.9 L, 0.580 mmol) at room temperature, the reaction was continued for 30 min at 60. After cooling to room temperature, 4-pentene-1-ol (0.90 mL, 8.701 mmol) dissolved in 2 mL of tetrahydrofuran was added. Then, after adding triethylamine (0.97 mL, 6.961 mmol) dissolved in 2 mL of tetrahydrofuran, the reaction was continued for 1 hr at 50. When the reaction was completed, saturated NaHCO$_3$ solution was added, and then the same was extracted with ethyl acetate. After drying over anhydrous MgSO$_4$, the crude product was purified by column chromatography on silica gel (hexane/ethyl acetate=1/2, v/v) to obtain 1.38 g (90.6%) of the target compound.

$^1$H NMR(300 MHz, CDCl$_3$) 1.82 (br, 4H), 2.95 (dd, 1H, J=16.6 Hz, J=7.9 Hz), 3.39 (dd 1H, J=16.6 Hz, J=10.2 Hz), 3.70 (br d, 2H), 3.89 (s, 6H), 4.74 (m, 1H), 6.83 (d, 1H), 7.00 (d 1H), 7.96 (s, 1H).

COMPARATIVE EXAMPLE 3

Preparation of 3-[3-(3,4-Dimethoxyphenyl)-4,5-dihydroisoxazol-5-yl]propanal

After dissolving pyridinium chlorochromate (PCC; 2.249 g, 10.435 mmol) and 70–230 mesh SiO$_2$ (2.748 g) in 25 mL of methylene chloride, 3-[3-(3,4-dimethoxyphenyl)-4,5-dihydroisoxazol-5-yl]propan-1-ol (1.374 g, 5.217 mmol) dissolved in 2 mL of methylene chloride was added. After the reaction was continued for about 6 hr, 10 mL of diethyl ether was added and the reaction mixture was filtered through a cellite bed. After removing all the solvent and purifying by column chromatography on silica gel (hexane/ethyl acetate=1.5/1, v/v), 0.72 g (51.6%) of the target compound was obtained.

$^1$H NMR(300 MHz, CDCl$_3$) 1.99 (m, 2H), 2.69 (t, 2H), 2.97 (dd, 1H, J=16.6 Hz, J=7.2 Hz), 3.43 (dd, 1H, J=16.6 Hz, J=10.3 Hz), 3.90 (s, 6H), 4,75 (m, 1H), 6.85 (d, 1H), 7.02 (d, 1H), 7.98 (s, 1H), 9.83 (s, 1H).

The following Examples are preparation examples of the compound represented by Formula (1) or its pharmaceutically acceptable addition salt.

EXAMPLE 1

Preparation of 1-Benzhydryl-4-{3-[3-(4-fluorophenyl)-4,5-dihydroisoxazol-5-yl]propyl}piperazine About 3 min after dissolving 1-(diphenylmethyl)piperazine (21.5 mg, 0.085 mmol) and 3-[3-(4-fluorophenyl)-4,5-dihydroisoxazol-5-yl]propanal (20.5 mg, 0.093 mmol) in 2 mL of dry methylene chloride, was added NaBH(OAc)$_3$ (52.7 mg, 0.248 mmol). After placing molecular sieves (5 beads) to remove water produced in the condensation process, the reaction was carried out for about 12 hr. When the reaction was completed, saturated NaHCO$_3$ solution was added, and then the same was extracted with 20 mL of diethyl ether. After drying the organic layer over anhydrous MgSO$_4$, the solvent was removed under reduced pressure. After dissolving the reaction mixture with 1 mL of diethyl ether, HCl ether solution was slowly dropped. White hydrochloric acid salt in the reaction container was obtained through filtration or centrifugation, and it was washed several times with diethyl ether. 22.6 mg (65.7%) of the target compound was obtained by drying the same under reduced pressure.

$^1$H NMR(300 MHz, CDCl$_3$) 1.44 (s, 1H), 1.68 (m, 5H), 2.44 (br, 10H), 2.94 (dd, 1H, J=16.4 Hz, J=8.1 Hz), 3.36 (dd, 1H, J=16.4 Hz, J=10.4 Hz), 4.22 (s, 1H), 4.75 (m, 1H), 7.23 (m, 8H), 7.50 (d, 4H), 7.65 (m, 2H).

EXAMPLE 2

Preparation of 1-Benzhydryl-4-{3-[3-(3-nitrophenyl)-4,5-dihydroisoxazol-5-yl]propyl}piperazine 3-[3-(3-nitrophenyl)-4,5-Dihydroisoxazol-5-yl]propanal (21.9 mg, 0.088 mmol), 1-(diphenylmethyl)piperazine (20.3 mg, 0.080 mmol), molecular sieves (5 beads), and NaBH(OAc)$_3$ (51.1 mg, 0.241 mmol) were reacted in 3 mL of methylene chloride for about 12 hr. With the following processes the same as in Example 1, 20.7 mg (48.4%) of the target compound was obtained.

$^1$H NMR(300 MHz, CDCl$_3$) 1.68 (br, 4H), 2.51 (br, 9H), 2.94 (dd, 1H, J=16.4 Hz, J=7.9 Hz), 3.69 (dd, 1H, J=16.4 Hz, J=10.2 Hz), 4.22 (s, 1H), 4.75 (m, 1H), 7.25 (m, 6H), 7.41 (d, 7H), 7.68 (m, 1H).

EXAMPLE 3

Preparation of 1-Benzhydryl4-{3-[3-(3,4-dimethoxyphenyl)-4,5-dihydroisoxazol-5-yl]propyl}piperazine 3-[3-(3,4-Dimethoxyphenyl)-4,5-dihydroisoxazol-5-yl]propanal (20.0 mg, 0.079 mmol), 1-(diphenylmethyl)piperazine (19.94 mg, 0.079 mmol), molecular sieve(5 beads) and NaBH(OAc)$_3$ (50.2 mg, 0.237 mmol) were reacted in 3 mL of methylene chloride for about 12 hr. With the following processes the same as in Example 1, 28.4 mg (72.0%) of the target compound was obtained.

$^1$H NMR(300 MHz, CDCl$_3$) 1.43 (s, 2H), 1.58 (br, 4H), 2.52 (br, 8H), 2.97 (dd, 1H, J=16.6 Hz, J=7.9 Hz), 3.18 (dd, 1H, J=16.6 Hz, J=10.2 Hz), 3.95 (s, 6H), 4.16 (s, 1H), 4.87 (m, 1H), 6.92 (d, 1H), 7.01 (d, 1H), 7.24 (m, 7H), 7.43 (d, 5H).

EXAMPLE 4

Preparation of 1-Benzhydryl4-[3-(3-phenyl-4,5-dihydroisoxazol-5-yl) propyl]piperazine 3-(3-Phenyl-4,5-dihydroisoxazol-5-yl)propanal (19.1 mg, 0.087 mmol), 1-(diphenylmethyl)piperazine (20.0 mg, 0.079 mmol), molecular sieve (5 beads) and NaBH(OAc)$_3$ (50.4 mg, 0.237 mmol) were reacted in 3 mL of methylene chloride for about 12 hr. With the following processes the same as in Example 1, 37.1 mg (96.8%) of the target compound was obtained.

$^1$H NMR(300 MHz, CDCl$_3$) 1.71 (m, 4H), 2.53 (br, 10H), 3.00 (dd, 1H, J=16.5 Hz, J=8.1 Hz), 3.43 (dd, 1H, J=16.6 Hz, J=10.5 Hz), 4.23 (s, 1H), 4.83 (m, 1H), 7.24 (m, 7H), 7.42 (d, 4H), 7.60 (t, 1H), 8.03 (d, 1H), 8.25 (d, 1H), 8.39 (s, 1H).

EXAMPLE 5

Preparation of 1-Benzhydryl4-{3-[3-(3-phenoxyphenyl)-4,5-dihydroisoxazol-5-yl]propyl}piperazine 3-[3-(3-Phenoxyphenyl)-4,5-dihydroisoxazol-5-yl]propanal (27.1 mg, 0.087 mmol), 1-(diphenylmethyl)

piperazine (20.0 mg, 0.078 mmol), molecular sieve (5 beads) and NaBH(OAc)$_3$ (50.0 mg, 0.237 mmol) were reacted in 3 mL of methylene chloride for about 12 hr. With the following processes the same as in Example 1, 20.2 mg (53.3%) of the target compound was obtained.

$^1$H NMR(200 MHz, CDCl$_3$) 1.30 (br, 1H), 1.71 (br, 5H), 2.56 (br, 8H), 2.94 (dd, 1H, J=16.6 Hz, J=8.2 Hz), 3.37 (dd, 1H, J=16.2 Hz, J=10.4 Hz), 4.25 (s, 1H), 4.77 (m, 1H), 7.23 (br m, 19H).

EXAMPLE 6

Preparation of 1-{3-[3-(3-nitrophenyl)-4,5-dihydroisoxazol-5-yl]propyl}4-phenylpiperazine 3-[3-(3-Nitrophenyl)-4,5-dihydroisoxazol-5-yl]propanal (33.7 mg, 0.135 mmol), 1-phenylpiperazine (20.0 mg, 0.123 mmol), molecular sieve (5 beads) and NaBH(OAc)$_3$ (78.4 mg, 0.369 mmol) were reacted in 3 mL of methylene chloride for about 12 hr. With the following processes the same as in Example 1, 28.4 mg (58.4%) of the target compound was obtained.

$^1$H NMR(200 MHz, CDCl$_3$) 1.85 (br, 4H), 2.69 (br, 8H), 3.07 (dd, 1H, J=16.6 Hz, J=8.2 Hz), 3.38 (dd, 1H, J=16.6 Hz, J=10.6 Hz), 3.71 (m, 2H), 4.92 (m, 2H), 6.91 (m, 3H), 7.28 (m, 2H), 7.62 (t, 1H), 8.09 (d, 1H), 8.27 (d, 1H), 8.43 (s, 1H).

EXAMPLE 7

Preparation of 1-{3-[3-(3,4-Dimethoxyphenyl)-4,5-dihydroisoxazol-5-yl]propyl}4-phenylpiperazine 3-[3-(3,4-Dimethoxyphenyl)-4,5-dihydroisoxazol-5-yl] propanal (36.3 mg, 0.135 mmol), 1-phenylpiperazine (20.0 mg, 0.123 mmol), molecular sieve (5 beads) and NaBH (OAc)$_3$ (78.4 mg, 0.369 mmol) were reacted in 3 mL of methylene chloride for about 12 hr. With the following processes the same as in Example 1, 45.5 mg (90.1%) of the target compound was obtained.

$^1$H NMR(300 MHz, CDCl$_3$) 1.65 (br, 4H), 2.46 (t, 2H), 2.62 (br s, 4H), 2.97 (dd, 1H, J=16.3 Hz, J=8.0 Hz), 3.20 (br s, 4H), 3.40 (dd, 1H, J=16.2 Hz, J=10.2 Hz), 3.91 (s, 6H), 4.78 (1H, m), 6.87 (m, 4H), 7.02 (d, 1H), 7.24 (m, 2H), 7.40 (s, 1H).

EXAMPLE 8

Preparation of 1-(2-Methoxyphenyl)-4-{3-[3-(3-nitrophenyl)-4,5-dihydroisoxazol-5-yl] propyl}piperazine 3-[3-(3-Nitrophenyl)-4,5-dihydroisoxazol-5-yl] propanal (23.8 mg, 0.096 mmol), 1-(2-methoxyphenyl)piperazine hydrochloride (20.0 mg, 0.087 mmol), molecular sieve (5 beads), NaBH(OAc)$_3$ (55.5 mg, 0.262 mmol) and diisopropylethylamine. (26.9 L, 0.087 mmol) were reacted in 3 mL of methylene chloride for about 12 hr. With the following processes the same as in Example 1, 31.2 mg (78.6%) of the target compound was obtained.

$^1$H NMR(200 MHz, CDCl$_3$) 1.78 (br, 4H), 2.56 (t, 2H), 2.73 (d, 4H), 3.06 (dd, 1H, J=16.6 Hz, J=8.2 Hz), 3.12 (s, 4H), 3.48 (dd, 1H, J=16.6 Hz, J=10.8 Hz), 3.87 (s, 3H), 4,91 (m, 1H), 6.93 (m, 4H), 7.61 (t, 1H), 8.10 (d, 1H), 8.33 (d, 1H), 8.42 (s, 1H).

EXAMPLE 9

Preparation of 1-{3-[3-(3,4-dimethoxyphenyl)-4,5-dihydroisoxazol-5-yl]propyl}-4-(2-methoxyphenyl) piperazine 3-[3-(3,4-Dimethoxyphenyl)-4,5-dihydroisoxazol-5-yl] propanal (25.8 mg, 0.096 mmol), 1-(2-methoxyphenyl) piperazine hydrochloride (20.0 mg, 0.087 mmol), molecular sieve (5 beads), NaBH(OAc)$_3$ (55.5 mg, 0.262 mmol) and diisopropylethylamine (26.9 L, 0.087 mmol) were reacted in 3 mL of methylene chloride for about 12 hr. With the following processes the same as in Example 1, 22.7 mg (60.0%) of the target compound was obtained.

$^1$H NMR(200 MHz, CDCl$_3$) 1.76 (m, 6H), 2.53 (t, 2H), 2.73 (d, 3H), 2.99 (dd, 1H, J=16.0 Hz, J=8.2 Hz), 3.13 (s, 3H), 3.41 (dd, 1H, J=16.0 Hz, J=10.4 Hz), 3.87 (s, 3H), 3.93 (s, 6H), 4.78 (m, 1H), 6.96 (m, 6H), 7.41 (s, 1H).

EXAMPLE 10

Preparation of 1-(2-Methoxyphenyl)-4-{3-[3-(thiophene-2-yl)-4,5-dihydroisoxazol-5-yl] propyl}piperazine 3-(3-(2-Thienyl)-4,5-dihydroisoxazol-5-yl)propanal (21.6 mg, 0.096 mmol), 1-(2-methoxyphenyl)piperazine hydrochloride (20.0 mg, 0.087 mmol), molecular sieve (5 beads), NaBH(OAc)$_3$ (55.5 mg, 0.262 mmol) and diisopropylethylamine (26.9 L, 0.087 mmol) were reacted in 3 mL of methylene chloride for about 12 hr. With the following processes the same as in Example 1, 31.0 mg (92.3%) of the target compound was obtained.

$^1$H NMR(200 MHz, CDCl$_3$) 1.76 (br, 4H), 2.50 (t, 2H), 2.71 (d, 4H), 3.01 (dd, 1H, J=16.6 Hz, J=8.4 Hz), 3.12 (s, 4H), 3.43 (dd, 1H, J=16.6 Hz, J=10.2 Hz), 3.87 (s, 3H), 4.77 (m, 1H), 6.97 (m, 6H), 7.31 (m, 1H).

EXAMPLE 11

Preparation of 1-(4-Fluorophenyl)4-{3-[3-(3-phenoxyphenyl)4,5-dihydroisoxazol-5-yl] propyl}piperazine 3-(3-(2-Phenoxyphenyl)-4,5-dihydroisoxazol-5-yl) propanal (38.0 mg, 0.122 mmol), 1-(4-fluorophenyl) piperazine (20.0 mg, 0.111 mmol), molecular sieve (5 beads) and NaBH(OAc)$_3$ (70.5 mg, 0.333mmol) were reacted in 3 mL of methylene chloride for about 12 hr. With the following processes the same as in Example 1, 28.7 mg (56.3%) of the target compound was obtained.

$^1$H NMR(200 MHz, CDCl$_3$) 1.24 (t, 2H), 1.75 (br, 4H), 2.48 (t, 1H), 2.64 (br, 3H), 2.98 (dd, 1H, J=16.0 Hz, J=8.2 Hz), 3.14 (br, 4H), 3.39 (dd, 1H, J=16.6 Hz, J=10.4 Hz), 4.80 (m, 1H), 7.02 (m, 7H), 7.34 (m, 6H).

EXAMPLE 12

Preparation of 1 (2-Fluorophenyl)-4-{3-[3-(3-nitrophenyl)4,5-dihydroisoxazol-5-yl] propyl}piperazine 3-[3-(3-Nitrophenyl)-4,5-dihydroisoxazol-5-yl]propanal (30.3 mg, 0.122 mmol), 1-(2-fluorophenyl)piperazine (20.0 mg, 0.111 mmol), molecular sieve (5 beads) and NaBH (OAc)$_3$ (70.5 mg, 0.333 mmol) were reacted in 3 mL of methylene chloride for about 12 hr. With the following processes the same as in Example 1, 20.8 mg (50.3%) of the target compound was obtained.

$^1$H NMR(200 MHz, CDCl$_3$) 1.78 (br, 4H), 2.53 (t, 2H), 2.70 (br, 4H), 3.96 (dd, 1H, J=16.6 Hz, J=8.4 Hz), 3.17 (br, 4H), 3.50 (dd, 1H, J=16.6 Hz, J=10.6 Hz), 4.90 (m, 1H), 7.01 (m, 4H), 7.62 (t, 1H), 8.10 (d, 1H), 8.27 (d, 1H), 8.43 (s, 1H).

EXAMPLE 13

Preparation of 1-(2-Fluorophenyl)4-(3-[3-(3-phenoxyphenyl)4,5-dihydroisoxazol-5-yl)propyl] piperazine 3-[3-(3-Phenoxyphenyl)-4,5-dihydroisoxazol-5-yl] propanal (38.0 mg, 0.122 mmol), 1-(2-fluorophenyl)

piperazine (20.0 mg, 0.111 mmol), molecular sieve (5 beads) and NaBH(OAc)$_3$ (70.5 mg, 0.333 mmol) were reacted in 3 mL of methylene chloride for about 12 hr. With the following processes the same as in Example 1, 35.5 mg (70.1 %) of the target compound was obtained.

$^1$H NMR(200 MHz, CDCl$_3$) 1.76 (br, 6H), 2.51 (t, 1H), 2.71 (d, 3H), 2.97 (dd, 1H, J=16.6 Hz, J=7.8 Hz), 3.15 (s, 4H), 3.39 (dd, 1H, J=16.6 Hz, J=10.4 Hz), 4.80 (m, 1H), 7.05 (m, 7H), 7.37 (t, 5H).

EXAMPLE 14

Preparation of 1-(2-Chlorophenyl)-4-[3-(3-phenyl-4, 5-dihydroisoxazol-5-yl)propyl]piperazine 3-(3-Phenyl-4,5-dihydroisoxazol-5-yl)propanal (20.7 mg, 0.094 mmol), 1-(2-chlorophenyl)piperazine hydrochloride (20.0 mg, 0.086 mmol), molecular sieve (5 beads), NaBH(OAc)$_3$ (54.5 mg, 0.257 mmol) and diisopropylethylamine (26.9 L, 0.085 mmol) were reacted in 3 mL of methylene chloride for about 12 hr. With the following processes the same as in Example 1, 25.8 mg (87.2%) of the target compound was obtained.

$^1$H NMR(200 MHz, CDCl$_3$) 1.76 (br, 4H), 2.49 (t, 1H), 2.67 (d, 3H), 3.01 (dd, 1H, J=16.6 Hz, J=8.4 Hz), 3.12 (br, 4H), 3.48 (dd, 1H, J=16.6 Hz, J=10.4 Hz), 3.53 (t, 2H), 4.81 (m, 1H), 7.02 (m, 2H), 7.17 (m, 1H), 7.40 (m, 4H), 7.68 (m, 2H).

EXAMPLE 15

Preparation of 2-(4-{3-[3-(3,4-Dimethoxyphenyl)-4, 5-dihydroisoxazol-5-yl]propyl}piperazine-1-yl) pyrimidine 3-[3-(3,4-Dimethoxyphenyl)-4,5-dihydroisoxazol-5-yl] propanal (24.9 mg, 0.092 mmol), 1-(2-pyrimidyl)piperazine dihydrochloride (20.0 mg, 0.084 mmol), molecular sieve (5 beads), NaBH(OAc)$_3$ (53.6 mg, 0.252 mmol) and diisopropylethylamine (53.9 L, 0.168 mmol) were reacted in 3 mL of methylene chloride for about 12 hr. With the following processes the same as in Example 1, 23.6 mg (68.2%) of the target compound was obtained.

$^1$H NMR(200 MHz, CDCl$_3$) 1.73 (br, 4H), 2.51 (br, 6H), 2.96 (dd, 1H, J=16.0 Hz, J=8.2 Hz), 3.41 (dd, 1H, J=16.0 Hz, J=10.4 Hz), 3.86 (t, 4H), 3.92 (s, 6H), 4.77 (m, 1H), 6.49 (t, 1H), 6.86 (d, 1H), 7.03 (d, 1H), 7.40 (s, 1H), 8.31 (d, 2H).

EXAMPLE 16

Preparation of 4-(4-Chlorophenyl)-1-[3-(3-phenyl-4, 5-dihydroisoxazol-5-yl)propyl]piperidine-4-ol 3-(3-Phenyl-4,5-dihydroisoxazol-5-yl)propanal (22.7 mg, 0.103 mmol), 4-(2-keto-1-benzimidazolinyl)piperazine (20.0 mg, 0.094 mmol), molecular sieve (5 beads) and NaBH(OAc)$_3$ (60.0 mg, 0.283 mmol) were reacted in 3 mL of methylene chloride for about 12 hr. With the following processes the same as in Example 1, 19.2 mg (51.1%) of the target compound was obtained.

$^1$H NMR(200 MHz, CDCl$_3$) 1.76 (br, 6H), 2.11 (br, 2H), 2.53 (s, 3H), 2.91 (d, 3H), 3.02 (dd, 1H, J=16.2 Hz, J=8.4 Hz), 3.43 (dd, 1H, J=16.6 Hz, J=10.2 Hz), 4.79 (m, 1H), 7.32 (d, 2H), 7.45 (d, 5H), 7.66 (s, 2H).

EXAMPLE 17

Preparation of 1-[3-(3-Phenyl4,5-dihydroisoxazol-5-yl)propyl]4-(2-methylphenyl)piperazine 3-(3-Phenyl-4,5-dihydroisoxazol-5-yl)propanal (27.3 mg, 0.124 mmol), 1-(o-tolyl) piperazine (20.0 mg, 0.113 mmol), molecular sieve (5 beads) and NaBH(OAc)$_3$ (72.1 mg, 0.340 mmol) were reacted in 3 mL of methylene chloride for about 12 hr. With the following processes the same as in Example 1, 30.1 mg (73.1%) of the target compound was obtained.

$^1$H NMR(200 MHz, CDCl$_3$) 1.77 (br, 6H), 2.32 (s, 3H), 2.56 (t, 1H), 2.71 (br, 3H), 3.00 (br, 4H), 3.05 (dd, 1H, J=16.6 Hz, J=8.2 Hz), 4.34 (dd, 1H, J=16.0 Hz, J=10.4 Hz), 4.81 (m, 1H), 7.04 (m, 1H), 7.19 (t, 1H), 7.43 (br, 4H), 7.68 (br, 3H).

EXAMPLE 18

Preparation of 1-[Bis(4-fluorophenyl)methyl]-4-{3-[3-(3-nitrophenyl)4,5-dihydroisoxazol-5-yl] propyl}piperazine 3-[3-(3-Nitrophenyl)-4,5-dihydroisoxazol-5-yl]propanal (19.3 mg, 0.077 mmol), 1-[bis(4-fluorophenyl)methyl] piperazine (20.4 mg, 0.070 mmol), molecular sieve (5 beads) and NaBH(OAc)$_3$ (45.0 mg, 0.212 mmol) were reacted in 3 mL of methylene chloride for about 12 hr. With the following processes the same as in Example 1, 23.8 mg (64.7%) of the target compound was obtained.

$^1$H NMR(200 MHz, CDCl$_3$) 1.72 (m, 4H), 2.53 (br, 8H), 3.03 (dd, 1H, J=16.6 Hz, J=8.0 Hz), 3.46 (dd, 1H, J=16.6 Hz, J=10.4 Hz), 3.65 (m, 1H), 3.77 (m, 1H), 4.25 (s, 1H), 4.86 (m, 1H), 6.98 (t, 4H), 7.33 (t, 4H), 7.60 (t, 1H), 8.07 (d, 1H), 8.32 (d, 1H), 8.42 (t, 1H).

EXAMPLE 19

Preparation of 1-{3-[3-(3,4-Dimethoxyphenyl)-4,5-dihydroisoxazol-5-yl]propyl}-4-(2-ethoxyphenyl) piperazine 3-[3-(3,4-Dimethoxyphenyl)-4,5-dihydroisoxazol-5-yl] propanal (22.96 mg, 0.090 mmol), 1-(2-ethoxyphenyl) piperazine hydrochloride (20.0 mg, 0.082 mmol), molecular sieve (5 beads), NaBH(OAc)$_3$ (52.4 mg, 0.247 mmol) and diisopropylethylamine (26.95 L, 0.082 mmol) were reacted in 3 mL of methylene chloride for about 12 hr. With the following processes the same as in Example 1, 22.9 mg (68.2%) of the target compound was obtained.

$^1$H NMR(200 MHz, CDCl$_3$) 1.26 (q, 2H), 1.44 (t, 3H), 1.73 (br, 4H), 2.27 (t, 2H), 2.61 (d, 3H), 2.98 (dd, 1H, J=16.6 Hz, J=7.8 Hz), 3.14 (s, 6H), 3.28 (dd, 1H, J=16.6 Hz, J=10.2 Hz), 3.92 (s, 6H), 4.11 (t, 2H), 4.77 (m, 1H), 6.94 (m, 6H), 7.40 (s, 1H).

EXAMPLE 20

Preparation of 1-(2-Ethoxyphenyl)-4-{3-[3-(thiophene-2-yl)4,5-dihydroisoxazol-5-yl] propyl}piperazine 3-(3-(2-Thienylphenyl)-4,5-dihydroisoxazol-5-yl) propanal (20.4 mg, 0.090 mmol), 1-(2-ethoxyphenyl) piperazine hydrochloride (20.0 mg, 0.082 mmol), molecular sieve (5 beads), NaBH(OAc)$_3$ (52.4 mg, 0.247 mmol) and diisopropylethylamine (26.95 L, 0.082 mmol) were reacted in 3 mL of methylene chloride for about 12 hr. With the following processes the same as in Example 1, 23.6 mg (79.7%) of the target compound was obtained.

$^1$H NMR(200 MHz, CDCl$_3$) 1.23 (t, 1H), 1.47 (t, 3H), 1.78 (br, 5H), 2.49 (t, 1H), 2.70 (br, 3H), 3.02 (dd, 1H, J=16.0 Hz, J=8.2 Hz), 3.15 (s, 4H), 3.44 (dd, 1H, J=16.6 Hz, J=10.2 Hz), 4.08 (q, 2H), 4.79 (m, 1H), 6.97 (m, 4H), 7.07 (t, 1H), 7.20 (d, 1H), 7.39 (d, 1H).

EXAMPLE 21

Preparation of 1-Benzhydryl-4-{4-[3-(4-fluorophenyl)-4,5-dihydroisoxazol-5-yl]butyl}piperazine 4-[3-(4-Fluorophenyl)-4,5-dihydroisoxazol-5-yl]butanal (27.0 mg, 0.114 mmol), 1-(diphenylmethyl)piperazine (26.3 mg, 0.104 mmol), molecular sieve (5 beads) and NaBH(OAc)$_3$ (66.3 mg, 0.313 mmol) were reacted in 3 mL of methylene chloride for about 12 hr. With the following processes the same as in Example 1, 32.0 mg (65.1%) of the target compound was obtained.

$^1$H NMR(200 MHz, CDCl$_3$) 1.63 (br, 6H), 2.43 (br, 8H), 2.97 (dd, 1H, J=16.2 Hz, J=8.2 Hz), 3.38 (dd, 1H, J=16.8 Hz, J=10.4 Hz), 4.25 (s, 1H), 4.75 (s, 1H), 7.19 (m, 7H), 7.29 (d, 3H), 7.67 (m, 2H).

EXAMPLE 22

Preparation of 1-Benzhydryl-4-{4-[3-(3-nitrophenyl)-4,5-dihydroisoxazol-5-yl]butyl}piperazine 4-[3-(3-Nitrophenyl)-4,5-dihydroisoxazol-5-yl]butanal (30.0 mg, 0.114 mmol), 1-(diphenylmethyl)piperazine (26.2 mg, 0.104 mmol), molecular sieve (5 beads) and NaBH(OAc)$_3$ (66.1 mg, 0.312 mmol) were reacted in 3 mL of methylene chloride 3 mL for about 12 hr. With the following processes the same as in Example 1, 28.4. mg (54.8%) of the target compound was obtained.

$^1$H NMR(200 MHz, CDCl$_3$) 1.64 (br, 8H), 2.44 (br, 8H), 3.01 (dd, 1H, J=16.6 Hz, J=8.4 Hz), 3.45 (dd, 1H, J=16.6 Hz, J=10.4 Hz), 4.25 (s, 1H), 4.83 (m, 1H), 7.23 (m, 6H), 7.43 (d, 4H), 7.62 (t, 1H), 8.09 (d, 1H), 8.26 (d, 1H), 8.41 (s, 1H).

EXAMPLE 23

Preparation of 1-Benzhydryl-4-{4-[3-(3,4-dimethoxyphenyl)-4,5-dihydroisoxazol-5-yl]butyl}piperazine 4-[3-(3,4-Dimethoxyphenyl)-4,5-dihydroisoxazol-5-yl]butanal (31.0 mg, 0.111 mmol), 1-(diphenylmethyl)piperazine (25.6 mg, 0.101 mmol), molecular sieve (5 beads) and NaBH(OAc)$_3$ (64.6 mg, 0.308 mmol) were reacted in 3 mL of methylene chloride for about 12 hr. With the following processes the same as in Example 1, 35.7 mg (68.4%) of the target compound was obtained.

$^1$H NMR(200 MHz, CDCl$_3$) 1.65 (br, 7H), 2.28 (br, 8H), 2.94 (dd, 1H, J=16.6 Hz, J=8.2 Hz), 3.35 (dd, 1H, J=16.6 Hz, J=10.2 Hz), 3.90 (s, 6H), 4.23 (s, 1H), 4.69 (m, 1H), 6.85 (d, 1H), 7.01 (d, 1H), 7.26 (m, 6H), 7.43 (br, 5H).

EXAMPLE 24

Preparation of 1-Phenyl-4-[4-(3-phenyl-4,5-dihydroisoxazol-5-yl)butyl]piperazine 4-(3-Phenyl-4,5-dihydroisoxazol-5-yl)butanal (29.4 mg, 0.135 mmol), 1-phenylpiperazine (20.0 mg, 0.123 mmol), molecular sieve (5 beads) and NaBH(OAc)$_3$ (78.4 mg, 0.369 mmol) were reacted in 3 mL of methylene chloride for about 12 hr. With the following processes the same as in Example 1, 35.7 mg (68.4%) of the target compound was obtained.

$^1$H NMR(200 MHz, CDCl$_3$) 1.64 (br, 6H), 2.48 (t, 2H), 2.67 (br, 4H), 2.99 (dd, 1H, J=16.6 Hz, J=8.2 Hz), 3.25 (br, 4H), 3.38 (dd, 1H, J=16.6 Hz, J=10.2 Hz), 4.78 (m, 1H), 6.92 (m, 3H), 7.30 (t, 2H), 7.42 (m, 3H), 7.69 (m, 2H).

EXAMPLE 25

Preparation of 1-{4-[3-(4-Fluorophenyl)-4,5-dihydroisoxazol-5-yl]butyl}-4-(2-methoxyphenyl)piperazine 4-[3-(4-Fluorophenyl)-4,5-dihydroisoxazol-5-yl]butanal (22.6 mg, 0.096 mmol), 1-(2-methoxyphenyl)piperazine hydrochloride (20.0 mg, 0.087 mmol), molecular sieve (5 beads), NaBH(OAc)$_3$ (55.6 mg, 0.262 mmol) and diisopropylethylamine (26.9 µL, 0.087 mmol) were reacted in 3 mL of methylene chloride for about 12 hr. With the following processes the same as in Example 1, 22.8 mg (70.4%) of the target compound was obtained.

$^1$H NMR(200 MHz, CDCl$_3$) 1.23 (t, 1H), 1.58 (br, 7H), 2.47 (t, 2H), 2.70 (d, 3H), 2.96 (dd, 1H, J=16.6 Hz, J=8.4 Hz), 3.12 (s, 3H), 3.39 (dd, 1H, J=16.6 Hz, J=10.4 Hz), 3.87 (s, 3H), 4.76 (m, 1H), 7.00 (m, 6H), 7.66 (m, 2H).

EXAMPLE 26

Preparation of 1-(2-Methoxyphenyl)-4-{4-[3-(3-nitrophenyl)-4,5-dihydroisoxazol-5-yl]butyl}piperazine 4-[3-(3-Nitrophenyl)-4,5-dihydroisoxazol-5-yl]butanal (25.2 mg, 0.096 mmol), 1-(2-methoxyphenyl)piperazine hydrochloride (20.0 mg, 0.087 mmol), molecular sieve (5 beads), NaBH(OAc)$_3$ (55.6 mg, 0.312 mmol) and diisopropylethylamine (26.9 L, 0.087 mmol) were reacted in 3 mL of methylene chloride for about 12 hr. With the following processes the same as in Example 1, 18.3 mg (44.6%) of the target compound was obtained.

$^1$H NMR(200 MHz, CDCl$_3$) 1.24 (m, 2H), 1.65 (br, 6H), 2.14 (t, 1H), 2.70 (br, 3H), 3.03 (dd, 1H, J=16.6 Hz, J=8.4 Hz), 3.12 (br, 4H), 3.47 (dd, 1H, J=16.2 Hz, J=10.2 Hz), 3.87 (s, 3H), 4.85 (m, 1H), 6.93 (m, 4H), 7.60 (t, 1H), 8.09 (d, 1H), 8.26 (d, 1H), 8.41 (s, 1H).

EXAMPLE 27

Preparation of 1-{4-[3-(3,4-Dimethoxyphenyl)4,5-dihydroisoxazol-5-yl]butyl}-4-(2-methoxyphenyl)piperazine 4-[3-(3,4-Dimethoxyphenyl)-4,5-dihydroisoxazol-5-yl]butanal (26.7 mg, 0.096 mmol), 1-(2-methoxyphenyl)piperazine hydrochloride (20.0 mg, 0.087 mmol), molecular sieve (5 beads), NaBH(OAc)$_3$ (55.6 mg, 0.262 mmol) and diisopropylethylamine (26.9 L, 0.087 mmol) were reacted in 3 mL of methylene chloride for about 12 hr. With the following processes the same as in Example 1, 26.5 mg (62.5%) of the target compound was obtained.

$^1$H NMR(200 MHz, CDCl3) 1.64 (br, 6H), 2.46 (t, 2H), 2.69 (br, 4H), 2.96 (dd, 1H, J=16.6 Hz, J=8.4 Hz), 3.12 (s, 4H), 3.39 (dd, 1H, J=16.6 Hz, J=10.2 Hz), 3.86 (s, 3H), 3.91 (s, 6H), 4.73 (m, 1H), 6.95 (br m, 6H), 7.41 (s, 1H).

EXAMPLE 28

Preparation of 1-(2-Methoxyphenyl)-4-{4-[3-(thiophene-2-yl)-4,5-dihydroisoxazol-5-yl]butyl}piperazine 4-[3-(2-Thienylphenyl)-4,5-dihydroisoxazol-5-yl]butanal (21.5 mg, 0.096 mmol), 1-(2-methoxyphenyl)piperazine hydrochloride (20.0 mg, 0.087 mmol), molecular sieve (5 beads), NaBH(OAc)$_3$ (55.6 mg, 0.262 mmol) and diisopropylethylamine (26.9 L, 0.087 mmol) were reacted in 3 mL of methylene chloride for about 12 hr. With the following processes the same as in Example 1, 18.3 mg (48.9%) of the target compound was obtained.

$^1$H NMR(200 MHz, CDCl$_3$) 1.24 (t, 3H), 1.64 (br, 5H), 2.47 (t, 1H), 2.70 (s, 3H), 2.98 (dd, 1H, J=16.2 Hz, J=8.2 Hz), 3.13 (s, 4H), 3.39 (dd, 1H, J=16.2 Hz, J=10.2 Hz), 3.89 (s, 3H), 4.76 (m, 1H), 6.96 (m, 4H), 7.19 (m, 1H), 7.29 (d, 1H), 7.39 (s, 1H).

EXAMPLE 29

Preparation of 1-(2-Methoxyphenyl)-[4-(3-phenyl-4, 5-dihydroisoxazol-5-yl)butyl]piperazine 4-(3-Phenyl-4,5-dihydroisoxazol-5-yl)butanal (20.9 mg, 0.096 mmol), 1-(2-methoxyphenyl)piperazine hydrochloride (20.0 mg, 0.087 mmol), molecular sieve (5 beads), NaBH(OAc)$_3$ (55.6 mg, 0.262 mmol) and diisopropylethylamine (26.9 L, 0.087 mmol) were reacted in 3 mL of methylene chloride for about 12 hr. With the following processes the same as in Example 1, 25.5 mg (69.2%) of the target compound was obtained.

$^1$H NMR(200 MHz, CDCl$_3$) 1.63 (br, 8H), 2.48 (t, 2H), 2.72 (d, 3H), 2.99 (dd, 1H J=16.2 Hz, J=8.2 Hz), 3.12 (s, 3H), 3.42 (dd, 1H, J=16.6 Hz, J=10.4 Hz), 3.87 (s, 3H), 4.76 (m, 1H), 6.94 (m, 4H), 7.42 (m, 3H), 7.68 (m, 2H).

EXAMPLE 30

Preparation of 1-(2-Methoxyphenyl)-[4-(3-styryl-4, 5-dihydroisoxazol-5-yl)butyl]piperazine 4-[3-(2-Phenylvinyl)-4,5-dihydroisoxazol-5-yl]butanal (23.4 mg, 0.096 mmol), 1-(2-methoxyphenyl)piperazine hydrochloride (20.0 mg, 0.087 mmol), molecular sieve (5 beads), NaBH(OAc)$_3$ (55.6 mg, 0.262 mmol) and diisopropylethylamine (26.9 L, 0.087 mmol) were reacted in 3 mL of methylene chloride for about 12 hr. With the following processes the same as in Example 1, 28.7 mg (73.2%) of the target compound was obtained.

$^1$H NMR(200 MHz, CDCl$_3$) 1.23 (t, 1H), 1.62 (br, 6H), 2.47 (t, 1H), 2.70 (d, 3H), 2.85 (dd, 1H, J=16.6 Hz, J=8.4 Hz), 3.13 (s, 4H), 3.27 (dd, 1H, J=16.6 Hz, J=10.4 Hz), 3.87 (s, 3H), 4.71 (m, 1H), 6.96 (m, 4H), 7.39 (br m, 5H).

EXAMPLE 31

Preparation of 1-(2-Chlorophenyl)-4-{4-[3-(thiophene-2-yl)4,5-dihydroisoxazol-5-yl]butyl}piperazine 4-(3-Phenyl-4,5-dihydroisoxazol-5-yl)butanal (20.5 mg, 0.094 mmol), 1-(2-chlorophenyl)piperazine hydrochloride (20.0 mg, 0.085 mmol), molecular sieve (5 beads), NaBH(OAc)$_3$ (54.5 mg, 0.257 mmol) and diisopropylethylamine (26.9 L, 0.085 mmol) were reacted in 3 mL of methylene chloride for about 12 hr. With the following processes the same as in Example 1, 24.7 mg (80.5%) of the target compound was obtained.

$^1$H NMR(200 MHz, CDCl$_3$) 1.22 (t, 2H), 1.60 (br, 2H), 2.45 (t, 2H), 2.66 (br, 4H), 2.99 (dd, 1H, J=16.2 Hz, J=8.2 Hz), 3.10 (br, 4H), 3.42 (dd, 1H, J=16.0 Hz, J=10.2 Hz), 3.45 (m, 3H), 4.76 (m, 1H), 7.01 (m, 2H), 7.23 (m, 5H), 7.68 (m, 2H).

EXAMPLE 32

Preparation of 1-[4-(3-Phenyl-4,5-dihydroisoxazol-5-yl)butyl]-4-(2-methylphenyl)piperazine 4-(3-Phenyl-4,5-dihydroisoxazol-5-yl)butanal (27.1 mg, 0.124 mmol), 1-(o-tolyl) piperazine (20.0 mg, 0.113 mmol), molecular sieve (5 beads) and NaBH(OAc)$_3$ (72.1 mg, 0.340 mmol) were reacted in 3 mL of methylene chloride for about 12 hr. With the following processes the same as in Example 1, 26.5 mg (67.3%) of the target compound was obtained.

$^1$H NMR(200 MHz, CDCl$_3$) 1.59 (br, 8H), 2.33 (s, 3H), 2.50 (t, 1H), 2.68 (br, 3H), 2.99 (br, 4H), 3.07 (dd, 1H, J=16.6 Hz, J=8.2 Hz), 3.40 (dd, 1H, J=16.6 Hz, J=10.4 Hz), 4.76 (m, 1H), 7.04 (m, 1H), 7.19 (t, 2H), 7.43 (br, 3H), 7.07 (br, 3H).

EXAMPLE 33

Preparation of 1-{4-[3-(3,4-Dimethoxyphenyl)-4,5-dihydroisoxazol-5-yl]butyl}-4-(2-ethoxyphenyl)piperazine 4-[3-(3,4-Dimethoxyphenyl)-4,5-dihydroisoxazol-5-yl]butanal (25.1 mg, 0.090 mmol), 1-(2-ethoxyphenyl)piperazine hydrochloride (20.0 mg, 0.082 mmol), molecular sieve (5 beads), NaBH(OAc)$_3$ (52.4 mg, 0.247 mmol) and diisopropylethylamine (26.9 L, 0.082 mmol) were reacted in 3 mL of methylene chloride for about 12 hr. With the following processes the same as in Example 1, 23.1 mg (66.7%) of the target compound was obtained.

$^1$H NMR(200 MHz, CDCl$_3$) 1.24 (t, 3H), 1.47 (q, 2H), 1.74 (br, 8H), 2.43 (t, 1H), 2.64 (br, 3H), 2.97 (dd, 1H, J=16.6 Hz, J=8.2 Hz), 3.15 (s, 4H), 3.39 (dd, 1H, J=16.6 Hz, J=10.4 Hz), 3.93 (s, 6H), 4.74 (m, 1H), 6.94 (m, 6H), 7.41 (s, 1H).

The novel compound of the present invention represented by Formula (1) can be prepared in various preparation forms. Hereunder is given some examples of preparation forms containing the compound of the present invention represented by Formula (1) as active components. However, they should not be construed as limiting the scope of the present invention.

PREPARATION 1

Tablet (Direct Pressurization)

After sieving 5.0 mg of the active component, 14.1 mg of lactose, 0.8 mg of crosphobidone USNF and 0.1 mg of magnesium stearate were mixed and pressurized to a tablet form.

PREPARATION 2

Tablet (Wet Fabrication)

After sieving 5.0 mg of the active component, 16.0 mg of lactose and 4.0 mg of starch were mixed. After adding an adequate amount of the solution obtained by dissolving 800.3 mg of polysolbate in pure water, the same was particulated. After drying and sieving the particulate, 2.7 mg of colloidal silicon dioxide and 2.0 mg of magnesium stearate were mixed. Then, the particulate was pressurized to a tablet form.

PREPARATION 3

Powder and Capsule

After sieving 5.0 mg of active component, 14.8 mg of lactose, 10.0 mg of polyvinylpyrrolidone and 0.2 mg of magnesium stearate were mixed. The mixture was filled in a hard gelatin capsule using an adequate device.

PREPARATION 4

Parenteral Injection

With 100 mg, of the active component, 180 mg of mannitol, 26 mg of Na$_2$HPO$_4$.12H$_2$O and 2974 mg of distilled water, a parenteral injection was prepared.

EXPERIMENTAL EXAMPLE

Test for the Binding Affinity to Dopamine Receptor

Binding affinities of the compounds for dopamine receptors were determined indirectly by their ability to displace radiolabeled ligand from cloned human dopamine receptors. Compounds were incubated in receptor suspension to compete with the. radiolabeled ligand. The receptor-bound radiolabeled ligand was separated by filtering through Wallac glass fiber filtermat (GF/C) using Inotech cell harvester of 96-well format. The radioactivity bound to filter was counted by Micro-β counter (Wallac).

The aliquots of cloned human dopamine receptors stored at −70° C. were suspended in assay buffer and the content of receptor in each aliquot was determined by Bio-Rad DC protein assay kit to give an optimal protein (receptor) concentration obtained by preliminary receptor binding assay. Receptor suspension adjusted to optimal concentration was aliquoted in proper volume for assay and stored at −70° C. Binding assays of every compound were performed in duplicate and each different buffer solution was used for optimal assay with each subtype of dopamine receptors. Receptor binding assays were carried out in 96-well plates.

Receptor suspension of 100 μl was incubated at 27° C. for 30–60 min in a final volume of 0.25 ml reaction mixture containing 50 μl of hot-ligand and 10 μl of test compound. First, binding affinities of test compounds toward receptors were sought at two different concentrations, 1 μl and 10 μl, and then IC50 were determined for selected final compounds with high binding affinities. Haloperidol was used as the reference drug for the comparison's purpose.

After incubation, the reaction mixture was washed with ice-cold 50 mM Tris-acetate buffer by rapid filtration using a Inotech cell harvester (Inotech, Switzerland) through Whatman GF/C glass fiber filter presoaked in the assay buffer. The filter was covered with MeltiLex, sealed in a sample bag followed by drying in the microwave, and counted by MicroBeta Plus(Wallac, Finland) at a counting efficiency of 30–40%.

The following Table 1 shows some exemplary compounds used in the experiment. However, the present invention is not limited to the examples. In Table 2 and Table 3, the binding affinity (% inhibition) of the novel compounds according to the present invention to dopamine receptors and $IC_{50}$ (nM) value are presented.

TABLE

| Compound No. | R₁ | R₂ | n | X |
|---|---|---|---|---|
| 1 | 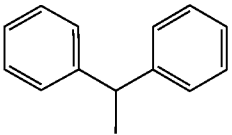 | 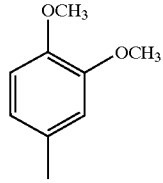 | 3 | N |
| 2 | 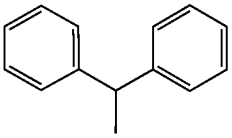 | 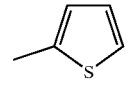 | 3 | N |
| 3 | 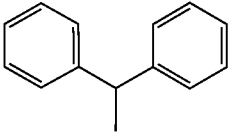 | 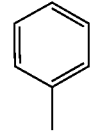 | 3 | N |
| 4 | 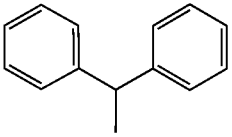 | 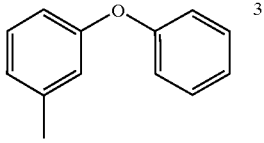 | 3 | N |
| 5 | 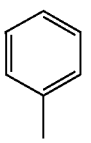 | 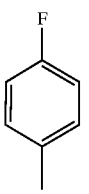 | 3 | N |

TABLE-continued
| Compound No. | R₁ | R₂ | n | X |
|---|---|---|---|---|
| 6 | 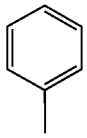 | 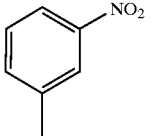 | 3 | N |
| 7 | 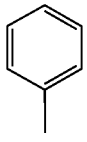 | 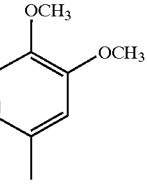 | 3 | N |
| 8 | 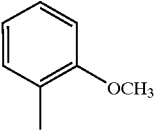 | 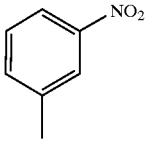 | 3 | N |
| 9 | 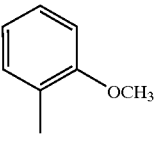 | 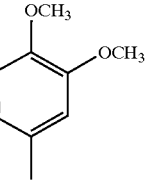 | 3 | N |
| 10 | 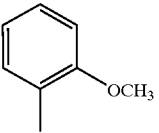 | 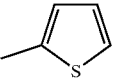 | 3 | N |
| 11 | 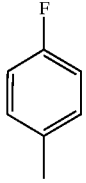 | 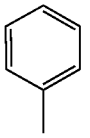 | 3 | N |
| 12 | 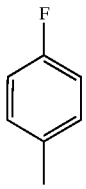 | 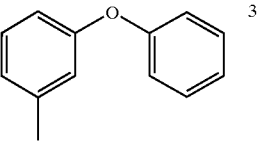 | 3 | N |
| 13 | 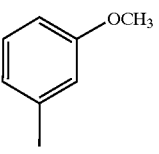 | 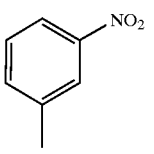 | 3 | N |

TABLE-continued
| Compound No. | R₁ | R₂ | n | X |
|---|---|---|---|---|
| 14 | 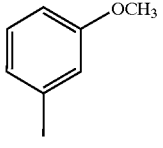 | 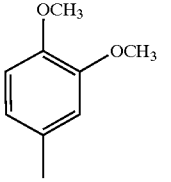 | 3 | N |
| 15 | 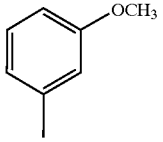 | 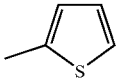 | 3 | N |
| 16 | 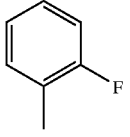 | 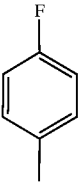 | 3 | N |
| 17 | 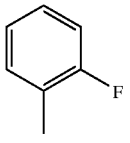 | 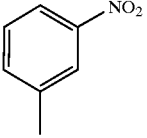 | 3 | N |
| 18 | 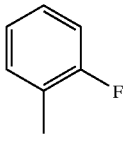 | 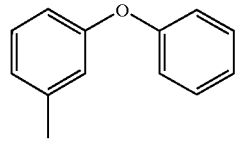 | 3 | N |
| 19 | 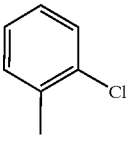 | 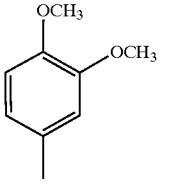 | 3 | N |
| 20 | 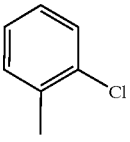 | 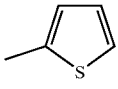 | 3 | N |
| 21 | 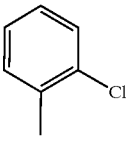 | 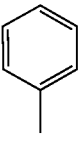 | 3 | N |
| 22 | 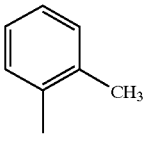 | 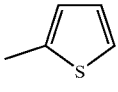 | 3 | N |

TABLE-continued
| Compound No. | R₁ | R₂ | n | X |
|---|---|---|---|---|
| 23 | 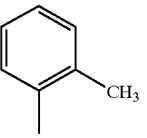 | 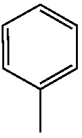 | 3 | N |
| 24 | 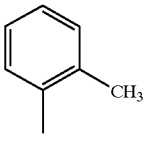 | 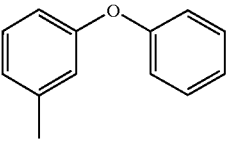 | 3 | N |
| 25 | 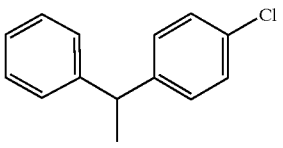 | 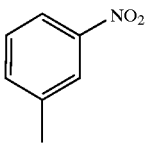 | 3 | N |
| 26 | 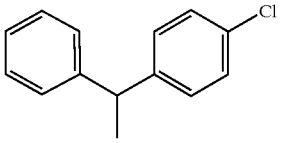 | 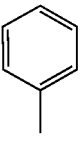 | 3 | N |
| 27 | 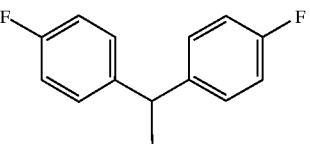 | 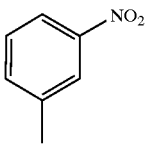 | 3 | N |
| 28 | 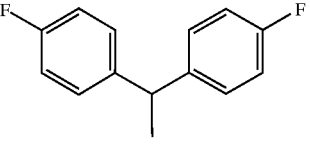 | 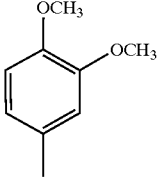 | 3 | N |
| 29 | 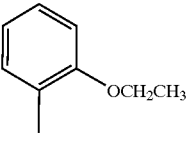 | 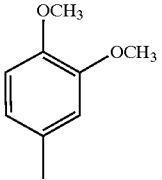 | 3 | N |
| 30 | 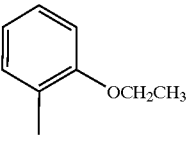 | 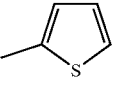 | 3 | N |
| 31 | 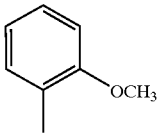 | 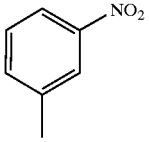 | 4 | N |

TABLE-continued

| Compound No. | R₁ | R₂ | n | X |
|---|---|---|---|---|
| 32 | 2-methoxyphenyl (with OCH₃) | 3,4-dimethoxyphenyl (OCH₃, OCH₃) | 4 | N |
| 33 | 2-methoxyphenyl (OCH₃) | 2-methylthiophene | 4 | N |
| 34 | 2-methoxyphenyl (OCH₃) | phenyl | 4 | N |

TABLE 2

Affinity to Dopamine Receptors (1 M)

| Items | Affinity to Dopamine Receptors (% Inhibition) | | | |
|---|---|---|---|---|
| | $D_1$ | $D_2$ | $D_3$ | $D_4$ |
| Compound No. 1 | 50.6 | 89.2 | 100.0 | 103.5 |
| Compound No. 2 | 33.4 | 78.2 | 89.3 | 102.7 |
| Compound No. 3 | 42.3 | 92.1 | 88.1 | 101.6 |
| Compound No. 4 | 40.0 | 85.8 | 82.6 | 103.1 |
| Compound No. 5 | <0.0 | 16.4 | 87.4 | 102.8 |
| Compound No. 6 | 14.5 | 42.6 | 77.4 | 100.2 |
| Compound No. 7 | 9.0 | 49.0 | 102.5 | 103.9 |
| Compound No. 8 | 28.2 | 75.0 | 91.1 | 103.5 |
| Compound No. 9 | 19.6 | 57.7 | 101.2 | 104.4 |
| Compound No. 10 | 19.9 | 56.0 | 99.9 | 103.6 |
| Compound No. 11 | 24.4 | 43.8 | 90.1 | 102.8 |
| Compound No. 12 | <0.0 | 81.0 | 92.6 | 102.6 |
| Compound No. 13 | 3.0 | 43.7 | 76.4 | 101.6 |
| Compound No. 14 | 10.5 | 41.6 | 99.6 | 103.1 |
| Compound No. 15 | 0.2 | 34.2 | 92.7 | 103.8 |
| Compound No. 16 | 17.5 | 59.2 | 102.2 | 104.4 |
| Compound No. 17 | 12.1 | 46.3 | 84.9 | 100.4 |
| Compound No. 18 | 8.9 | 51.1 | 96.3 | 104.1 |
| Compound No. 19 | 25.9 | 50.0 | 101.6 | 104.0 |
| Compound No. 20 | <0.0 | 18.4 | 95.7 | 103.5 |
| Compound No. 21 | 18.3 | 63.1 | 102.1 | 103.7 |
| Compound No. 22 | 6.0 | 48.7 | 95.7 | 100.6 |
| Compound No. 23 | 11.1 | 53.2 | 98.3 | 103.4 |
| Compound No. 24 | 15.9 | 76.6 | 95.8 | 102.2 |
| Compound No. 25 | 55.6 | 99.2 | 87.3 | 104.0 |
| Compound No. 26 | 56.4 | 95.0 | 93.4 | 104.0 |
| Compound No. 27 | 54.7 | 94.3 | 83.7 | 102.6 |
| Compound No. 28 | 63.5 | 96.7 | 102.0 | 104.8 |
| Compound No. 29 | 40.1 | 83.5 | 102.3 | 57.4 |
| Compound No. 30 | 57.8 | 88.2 | 101.2 | 102.3 |
| Compound No. 31 | 36.5 | 85.5 | 93.1 | 100.9 |
| Compound No. 32 | 27.9 | 72.6 | 82.5 | 100.2 |
| Compound No. 33 | 19.4 | 65.5 | 90.9 | 102.4 |
| Compound No. 34 | 23.6 | 58.3 | 83.8 | 100.1 |
| Haloperidol | 71.2 | 95.2 | 56.4 | 94.1 |

TABLE 3

$IC_{50}$ for Dopamine Receptors (nM)

| Items | $D_1$ | $D_2$ | $D_3$ | $D_4$ |
|---|---|---|---|---|
| Compound No. 7 | — | 9230 | 21 | 71 |
| Compound No. 9 | — | 1440 | 5 | 23 |
| Compound No. 10 | — | 1930 | 19 | 34 |
| Compound No. 14 | — | 8370 | 18 | 101 |
| Compound No. 19 | — | 5200 | 21 | 51 |
| Compound No. 28 | | | | |
| Racemic | — | 1710 | 4 | 368 |
| (+)-Isomer | — | — | 8 | 663 |
| (−)-Isomer | — | — | 85 | 483 |
| Compound No. 29 | | | | |
| Racemic | — | 110 | 2 | 108 |
| (+)-Isomer | — | — | 5 | 789 |
| (−)-Isomer | — | — | 8 | 149 |
| Compound No. 30 | | | | |
| Racemic | — | 470 | 4 | 11 |
| (+)-Isomer | — | — | 6 | 50 |
| (−)-Isomer | — | — | 33 | 228 |
| Haloperidol | — | 80 | 57 | 65 |

As explained above, since the compound according to the present invention represented by Formula (1) has superior and selective inhibitory activity against dopamine $D_3$ or $D_4$ receptors, it may be effective in the treatment of schizophrenia in mental disease.

What is claimed is:

1. A method of treating schizophrenia which comprises administering to a patient an effective amount of at least one 4,5-dihydroisoxazolylalkylpiperazine derivative represented by the following formula (1), or a pharmaceutically acceptable addition salt thereof, in racemic form or as individual optical isomers:

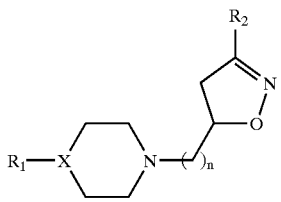

(1)

wherein R₁ represents at least one substituent of the group consisting of an aryl group, a phenylmethyl group, a diphenylmethyl group, and pyrimidinyl group, and wherein the substituent may have one or more further substituents selected from the group consisting of $C_1$–$C_6$ alkyl group, $C_1$–$C_6$ alkoxy group, a fluorine atom and a chlorine atom;

R₂ represents at least one substituent selected from the group consisting of an aryl group, a styryl group, and a thiophene group, and wherein the substituent may have at least one further substituent, selected from the group consisting of a fluorine atom, a nitro group, a $C_1$–$C_6$ alkyl group, a $C_1$–$C_6$ alkoxy group and a phenoxy group;

X represents CH or a nitrogen atom; and n represents 3 or 4.

2. A method according to claim 1, wherein said compound is at least one member selected from the group consisting of:

1-benzhydryl-4-{3-[3-(4-fluorophenyl)-4,5-dihydroisoxazol-5-yl]propyl}piperazine;

1-benzhydryl-4-{3-[3-(3-nitrophenyl)-4,5-dihydroisoxazol-5-yl]propyl}piperazine;

1-benzhydryl-4-{3-[3-(3,4-dimethoxyphenyl)-4,5-dihydroisoxazol-5-yl]propyl}piperazine;

1-benzhydryl-4-[3-(3-phenyl-4,5-dihydroisoxazol-5-yl)propyl]piperazine;

1-benzhydryl-4-{3-[3-(3-phenoxyphenyl)-4,5-dihydroisoxazol-5-yl]propyl}piperazine;

1-{3-[3-(3-nitrophenyl)-4,5-dihydroisoxazol-5-yl]propyl}-4-phenylpiperazine;

1-{3-[3-(3,4-dimethoxyphenyl)-4,5-dihydroisoxazol-5-yl]propyl}-4-phenylpiperazine;

1-(2-methoxyphenyl)-4-{3-[3-(3-nitrophenyl)-4,5-dihydroisoxazol-5-yl]propyl}piperazine;

1-{3-[3-(3,4-dimethoxyphenyl)-4 5-dihydroisoxazol-5-yl]propyl}-4-(2-methoxyphenyl)piperazine;

1-(2-methoxyphenyl)-4-{3-[3-(thiophene-2-yl)-4,5-dihydroisoxazol-5-yl]propyl}piperazine;

1-(4-fluorophenyl)-4-{3-[3-(3-phenoxyphenyl)-4,5-dihydroisoxazol-5-yl]propyl}piperazine;

1-(2-fluorophenyl)-4-{3-[3-(3-nitrophenyl)-4,5-dihydroisoxazol-5-yl]propyl}piperazine;

1-(2-fluorophenyl)-4-{3-[3-(3-phenoxyphenyl)-4,5-dihydroisoxazol-5-yl]propyl}piperazine;

1-(2-chlorophenyl)-4-[3-(3-phenyl-4,5-dihydroisoxazol-5-yl)propyl]piperazine;

2-(4-{3-[3-(3,4-dimethoxyphenyl)-4,5-dihydroisoxazol-5-yl]propyl}piperazine-1-yl)pyrimidine;

4-(4-chlorophenyl)-1-[3-(3-phenyl-4,5-dihydroisoxazol-5-yl)propyl]piperidine-4-ol;

1-[3-(3-phenyl-4,5-dihydroisoxazol-5-yl)propyl]-4-(2-methylphenyl)piperazine;

1-[bis(4-fluorophenyl)methyl]-4-{3-[3-(3-nitrophenyl)-4,5-dihydroisoxazol-5-yl]propyl}piperazine;

1-{3-[3-(3,4-dimethoxyphenyl)-4,5-dihydroisoxazol-5-yl]propyl}-4-(2-ethoxyphenyl)piperazine;

1-(2-ethoxyphenyl)-4-{3-[3-(thiophene-2-yl)-4,5-dihydroisoxazol-5-yl]propyl}piperazine;

1-benzhydryl-4-{4-[3-(4-fluorophenyl)-4,5-dihydroisoxazol-5-yl]butyl}piperazine;

1-benzhydryl-4-{4-[3-(3-nitrophenyl)-4,5-dihydroisoxazol-5-yl]butyl}piperazine;

1-benzhydryl-4-{4-[3-(3,4-dimethoxyphenyl)-4,5-dihydroisoxazol-5-yl]butyl}piperazine;

1-phenyl-4-[4-(3-phenyl-4,5-dihydroisoxazol-5-yl)butyl]piperazine;

1-{4-[3-(4-fluorophenyl)-4,5-dihydroisoxazol-5-yl]butyl}-4-(2-methoxyphenyl)piperazine;

1-(2-methoxyphenyl)-4-{4-[3-(3-nitrophenyl)-4,5-dihydroisoxazol-5-yl]butyl}piperazine;

1-{4-[3-(3,4-dimethoxyphenyl)-4,5-dihydroisoxazol-5-yl]butyl}-4-(2-methoxyphenyl)piperazine;

1-(2-methoxyphenyl)-4-{4-[3-(thiophene-2-yl)-4,5-dihydroisoxazol-5-yl]butyl}piperazine;

1-(2-methoxyphenyl)-[4-(3-phenyl-4,5-dihydroisoxazol-5-yl)butyl]piperazine;

1-(2-methoxyphenyl)-[4-(3-styryl-4,5-dihydroisoxazol-5-yl)butyl]piperazine;

1-(2-chlorophenyl)-4-{4-[3-(thiophene-2-yl)-4,5-dihydroisoxazol-5-yl]butyl}piperazine;

1-[4-(3-phenyl-4,5-dihydroisoxazol-5-yl)butyl]-4-(2-methylphenyl)piperazine;

1-{4-[3-(3,4-dimethoxyphenyl)-4,5-dihydroisoxazol-5-yl]butyl}-4-(2-ethoxyphenyl)piperazine; and pharmaceutically acceptable salt(s) thereof.

3. A method as claimed in claim 1 wherein said active ingredient(s) is formulated with at least one pharmaceutically acceptable carrier.

4. A method as claimed in claim 1 further comprising administering said compound(s) in a dosage of about 0.01 to 400 mg per day.

5. A method as claimed in claim 1 further comprising administering said composition in the form of a tablet, capsule, troches, liquid solution, or emulsion.

* * * * *